(12) United States Patent
Dunning et al.

(10) Patent No.: US 8,235,980 B2
(45) Date of Patent: Aug. 7, 2012

(54) ELECTROSURGICAL SYSTEM FOR MEASURING CONTACT QUALITY OF A RETURN PAD

(75) Inventors: James E. Dunning, Lafayette, CO (US); Jeffrey L. Eggleston, Broomfield, CO (US); Kyle R. Rick, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/326,040

(22) Filed: Dec. 14, 2011

(65) Prior Publication Data

US 2012/0089140 A1  Apr. 12, 2012

Related U.S. Application Data

(62) Division of application No. 11/800,687, filed on May 7, 2007, now Pat. No. 8,080,007.

(51) Int. Cl.
*A61B 18/16* (2006.01)
(52) U.S. Cl. ............................................. 606/32; 606/35
(58) Field of Classification Search .................... 606/32, 606/34–35
See application file for complete search history.

(56) References Cited

U.S. PATENT DOCUMENTS

| | | |
|---|---|---|
| 2,536,271 A | 1/1951 | Fransen et al. |
| 3,380,445 A | 4/1968 | Frasier |
| 3,534,306 A | 10/1970 | Watrous et al. |
| 3,543,760 A | 12/1970 | Bolduc |
| 3,642,008 A | 2/1972 | Bolduc |
| 3,683,923 A | 8/1972 | Anderson |
| 3,812,861 A | 5/1974 | Peters |
| 3,913,583 A | 10/1975 | Bross |
| 3,923,063 A | 12/1975 | Andrews et al. |
| 3,933,157 A | 1/1976 | Bjurwill et al. |
| 3,987,796 A | 10/1976 | Gonser |
| 4,067,342 A | 1/1978 | Burton |
| 4,092,985 A | 6/1978 | Kaufman |
| 4,094,320 A | 6/1978 | Newton et al. |
| 4,102,341 A | 7/1978 | Ikuno et al. |
| 4,114,622 A | 9/1978 | Gonser |
| 4,117,846 A | 10/1978 | Williams |
| 4,121,590 A | 10/1978 | Gonser |
| 4,126,137 A | 11/1978 | Archibald |

(Continued)

FOREIGN PATENT DOCUMENTS

CA  1219642  3/1987

(Continued)

OTHER PUBLICATIONS

U.S. Appl. No. 10/609,946, filed Jun. 30, 2003, Jeffrey L. Eggleston.

(Continued)

*Primary Examiner* — Linda Dvorak
*Assistant Examiner* — Jaymi Della

(57) ABSTRACT

A return pad includes a backing, at least one return electrode, and at least one ring sensor. The backing has a top side, a bottom side, and a periphery. The return electrode is disposed on the bottom side of the backing layer and is adapted to connect to a current generator. The ring sensor(s) is disposed in substantial concentric registration with the periphery of the backing and is configured to connect to a measuring component. The measuring component is operable to approximate contact quality of the return electrode during electrosurgical application and is configured to communicate with the generator.

10 Claims, 12 Drawing Sheets

U.S. PATENT DOCUMENTS

| | | | |
|---|---|---|---|
| 4,166,465 A | 9/1979 | Esty et al. | |
| 4,188,927 A | 2/1980 | Harris | |
| 4,200,104 A | 4/1980 | Harris | |
| 4,200,105 A | 4/1980 | Gonser | |
| 4,213,463 A | 7/1980 | Osenkarski | |
| 4,231,372 A | 11/1980 | Newton | |
| 4,237,887 A | 12/1980 | Gonser | |
| 4,253,721 A | 3/1981 | Kaufman | |
| 4,303,073 A | 12/1981 | Archibald | |
| 4,304,235 A | 12/1981 | Kaufman | |
| 4,331,149 A | 5/1982 | Gonser | |
| 4,343,308 A | 8/1982 | Gross | |
| 4,381,789 A | 5/1983 | Naser et al. | |
| 4,384,582 A | 5/1983 | Watt | |
| 4,387,714 A | 6/1983 | Geddes et al. | |
| 4,393,584 A | 7/1983 | Bare et al. | |
| 4,416,276 A | 11/1983 | Newton et al. | |
| 4,416,277 A | 11/1983 | Newton et al. | |
| 4,437,464 A | 3/1984 | Crow | |
| 4,494,541 A | 1/1985 | Archibald | |
| 4,494,552 A | 1/1985 | Heath | |
| 4,643,193 A | 2/1987 | DeMarzo | |
| 4,657,015 A | 4/1987 | Irnich | |
| 4,658,819 A | 4/1987 | Harris et al. | |
| 4,662,369 A | 5/1987 | Ensslin | |
| 4,669,468 A | 6/1987 | Cartmell et al. | |
| 4,699,146 A | 10/1987 | Sieverding | |
| 4,722,761 A | 2/1988 | Cartmell et al. | |
| 4,725,713 A | 2/1988 | Lehrke | |
| 4,741,334 A | 5/1988 | Irnich | |
| 4,745,918 A | 5/1988 | Feucht | |
| 4,748,983 A | 6/1988 | Shigeta et al. | |
| 4,750,482 A | 6/1988 | Sieverding | |
| 4,754,757 A | 7/1988 | Feucht | |
| 4,768,514 A | 9/1988 | DeMarzo | |
| 4,770,173 A | 9/1988 | Feucht et al. | |
| 4,788,977 A | 12/1988 | Farin et al. | |
| 4,799,480 A | 1/1989 | Abraham et al. | |
| 4,807,621 A | 2/1989 | Hagen et al. | |
| 4,844,063 A | 7/1989 | Clark | |
| 4,848,335 A | 7/1989 | Manes | |
| 4,852,571 A | 8/1989 | Gadsby et al. | |
| 4,862,889 A | 9/1989 | Feucht | |
| 4,873,974 A | 10/1989 | Hagen et al. | |
| 4,878,493 A | 11/1989 | Pasternak et al. | |
| 4,887,047 A | 12/1989 | Somerville | |
| 4,895,169 A | 1/1990 | Heath | |
| 4,933,535 A | 6/1990 | Zabinski | |
| 4,942,313 A | 7/1990 | Kinzel | |
| 4,947,846 A | 8/1990 | Kitagawa et al. | |
| 4,955,381 A | 9/1990 | Way et al. | |
| 4,961,047 A | 10/1990 | Carder | |
| 4,969,885 A | 11/1990 | Farin | |
| 5,000,753 A | 3/1991 | Hagen et al. | |
| 5,004,425 A | 4/1991 | Hee | |
| 5,010,896 A | 4/1991 | Westbrook | |
| 5,038,796 A | 8/1991 | Axelgaard et al. | |
| 5,042,981 A | 8/1991 | Gross | |
| 5,061,914 A | 10/1991 | Busch et al. | |
| 5,087,257 A | 2/1992 | Farin et al. | |
| 5,114,424 A * | 5/1992 | Hagen et al. | 606/32 |
| 5,152,762 A | 10/1992 | McElhenney | |
| 5,160,334 A | 11/1992 | Billings et al. | |
| 5,196,008 A | 3/1993 | Kuenecke et al. | |
| 5,246,439 A | 9/1993 | Hebborn et al. | |
| 5,271,417 A | 12/1993 | Swanson et al. | |
| 5,276,079 A | 1/1994 | Duan et al. | |
| 5,286,255 A | 2/1994 | Weber | |
| 5,312,401 A | 5/1994 | Newton et al. | |
| 5,336,255 A | 8/1994 | Kanare et al. | |
| 5,352,315 A | 10/1994 | Carrier et al. | |
| 5,362,420 A | 11/1994 | Itoh et al. | |
| 5,370,645 A | 12/1994 | Klicek et al. | |
| 5,372,596 A | 12/1994 | Klicek et al. | |
| 5,385,679 A | 1/1995 | Uy et al. | |
| 5,388,490 A | 2/1995 | Buck | |
| 5,389,376 A | 2/1995 | Duan et al. | |
| 5,390,382 A | 2/1995 | Hannant et al. | |
| 5,409,966 A | 4/1995 | Duan et al. | |
| 5,447,513 A | 9/1995 | Davison et al. | |
| 5,449,365 A | 9/1995 | Green et al. | |
| 5,452,725 A | 9/1995 | Martenson | |
| 5,480,399 A | 1/1996 | Hebborn | |
| 5,496,312 A | 3/1996 | Klicek | |
| 5,496,363 A | 3/1996 | Burgio et al. | |
| 5,520,180 A | 5/1996 | Uy et al. | |
| 5,536,446 A | 7/1996 | Uy et al. | |
| 5,540,684 A | 7/1996 | Hassler, Jr. | |
| 5,585,756 A | 12/1996 | Wang | |
| 5,599,347 A | 2/1997 | Hart et al. | |
| 5,601,618 A | 2/1997 | James | |
| 5,611,709 A | 3/1997 | McAnulty | |
| 5,632,280 A | 5/1997 | Leyde et al. | |
| 5,633,578 A | 5/1997 | Eggers et al. | |
| 5,643,319 A | 7/1997 | Green et al. | |
| 5,660,892 A | 8/1997 | Robbins et al. | |
| 5,670,557 A | 9/1997 | Dietz et al. | |
| 5,674,561 A | 10/1997 | Dietz et al. | |
| 5,678,545 A | 10/1997 | Stratbucker | |
| 5,688,269 A | 11/1997 | Newton et al. | |
| 5,695,494 A | 12/1997 | Becker | |
| 5,707,369 A | 1/1998 | Vaitekunas et al. | |
| 5,718,719 A | 2/1998 | Clare et al. | |
| 5,720,744 A | 2/1998 | Eggleston et al. | |
| 5,766,165 A | 6/1998 | Gentelia et al. | |
| 5,779,632 A | 7/1998 | Dietz et al. | |
| 5,797,902 A | 8/1998 | Netherly | |
| 5,800,426 A | 9/1998 | Taki et al. | |
| 5,817,091 A | 10/1998 | Nardella et al. | |
| 5,830,212 A | 11/1998 | Cartmell et al. | |
| 5,836,942 A | 11/1998 | Netherly et al. | |
| 5,846,558 A | 12/1998 | Nielsen et al. | |
| 5,853,750 A | 12/1998 | Dietz et al. | |
| 5,868,742 A | 2/1999 | Manes et al. | |
| 5,924,983 A | 7/1999 | Takaki et al. | |
| 5,947,961 A | 9/1999 | Netherly | |
| 5,952,398 A | 9/1999 | Dietz et al. | |
| 5,971,981 A | 10/1999 | Hill et al. | |
| 5,976,128 A | 11/1999 | Schilling et al. | |
| 5,983,141 A | 11/1999 | Sluijter et al. | |
| 5,985,990 A | 11/1999 | Kantner et al. | |
| 5,999,061 A | 12/1999 | Pope et al. | |
| 6,007,532 A | 12/1999 | Netherly | |
| 6,010,054 A | 1/2000 | Johnson et al. | |
| 6,026,323 A | 2/2000 | Skladnev et al. | |
| 6,030,381 A | 2/2000 | Jones et al. | |
| 6,032,063 A | 2/2000 | Hoar et al. | |
| 6,039,732 A | 3/2000 | Ichikawa et al. | |
| 6,053,910 A | 4/2000 | Fleenor | |
| RE36,720 E | 5/2000 | Green et al. | |
| 6,059,778 A | 5/2000 | Sherman | |
| 6,063,075 A | 5/2000 | Mihori | |
| 6,083,221 A | 7/2000 | Fleenor et al. | |
| 6,086,249 A | 7/2000 | Urich | |
| 6,121,508 A | 9/2000 | Bischof et al. | |
| 6,135,953 A | 10/2000 | Carim | |
| 6,171,304 B1 | 1/2001 | Netherly et al. | |
| 6,200,314 B1 | 3/2001 | Sherman | |
| 6,203,541 B1 | 3/2001 | Keppel | |
| 6,214,000 B1 | 4/2001 | Fleenor et al. | |
| 6,232,366 B1 | 5/2001 | Wang et al. | |
| 6,240,323 B1 | 5/2001 | Calenzo, Sr. et al. | |
| 6,246,912 B1 | 6/2001 | Sluijter et al. | |
| 6,258,085 B1 | 7/2001 | Eggleston | |
| 6,258,087 B1 | 7/2001 | Edwards et al. | |
| 6,275,786 B1 | 8/2001 | Daners | |
| 6,283,987 B1 | 9/2001 | Laird et al. | |
| 6,301,500 B1 | 10/2001 | Van Herk et al. | |
| 6,310,611 B1 | 10/2001 | Caldwell | |
| 6,347,246 B1 | 2/2002 | Perrault et al. | |
| 6,350,264 B1 | 2/2002 | Hooven | |
| 6,350,276 B1 | 2/2002 | Knowlton | |
| 6,355,031 B1 | 3/2002 | Edwards et al. | |
| 6,356,779 B1 | 3/2002 | Katzenmaier et al. | |
| 6,357,089 B1 | 3/2002 | Koguchi et al. | |
| 6,358,245 B1 | 3/2002 | Edwards et al. | |
| 6,379,161 B1 | 4/2002 | Ma | |

| | | |
|---|---|---|
| 6,409,722 B1 | 6/2002 | Hoey et al. |
| 6,413,255 B1 | 7/2002 | Stern |
| 6,415,170 B1 | 7/2002 | Loutis et al. |
| 6,454,764 B1 | 9/2002 | Fleenor et al. |
| 6,488,678 B2 | 12/2002 | Sherman |
| 6,511,478 B1 | 1/2003 | Burnside et al. |
| 6,537,272 B2 | 3/2003 | Christopherson et al. |
| 6,544,258 B2 | 4/2003 | Fleenor et al. |
| 6,546,270 B1 | 4/2003 | Goldin et al. |
| 6,565,559 B2 | 5/2003 | Eggleston |
| 6,569,160 B1 | 5/2003 | Goldin et al. |
| 6,582,424 B2 | 6/2003 | Fleenor et al. |
| 6,666,859 B1 | 12/2003 | Fleenor et al. |
| 6,669,073 B2 | 12/2003 | Milliman et al. |
| 6,736,810 B2 | 5/2004 | Hoey et al. |
| 6,796,828 B2 | 9/2004 | Ehr et al. |
| 6,799,063 B2 | 9/2004 | Carson |
| 6,830,569 B2 | 12/2004 | Thompson et al. |
| 6,849,073 B2 | 2/2005 | Hoey et al. |
| 6,860,881 B2 | 3/2005 | Sturm |
| 6,875,210 B2 | 4/2005 | Refior et al. |
| 6,892,086 B2 | 5/2005 | Russell |
| 6,905,497 B2 | 6/2005 | Truckai et al. |
| 6,939,344 B2 | 9/2005 | Kreindel |
| 6,948,503 B2 | 9/2005 | Refior et al. |
| 6,953,139 B2 | 10/2005 | Milliman et al. |
| 6,958,463 B1 | 10/2005 | Kochman et al. |
| 6,959,852 B2 | 11/2005 | Shelton, IV et al. |
| 6,979,329 B2 | 12/2005 | Burnside et al. |
| 6,997,735 B2 | 2/2006 | Ehr et al. |
| 7,025,765 B2 | 4/2006 | Balbierz et al. |
| 7,112,201 B2 | 9/2006 | Truckai et al. |
| 7,128,253 B2 | 10/2006 | Mastri et al. |
| 7,137,980 B2 | 11/2006 | Buysse et al. |
| 7,143,926 B2 | 12/2006 | Shelton, IV et al. |
| 7,160,293 B2 | 1/2007 | Sturm et al. |
| 7,166,102 B2 | 1/2007 | Fleenor et al. |
| 7,169,144 B2 | 1/2007 | Hoey et al. |
| 7,169,145 B2 | 1/2007 | Isaacson et al. |
| 7,182,604 B2 | 2/2007 | Ehr et al. |
| 7,220,260 B2 | 5/2007 | Fleming et al. |
| 7,229,307 B2 | 6/2007 | Ehr et al. |
| 7,258,262 B2 | 8/2007 | Mastri et al. |
| 7,267,675 B2 | 9/2007 | Stern et al. |
| 7,278,562 B2 | 10/2007 | Mastri et al. |
| 7,303,107 B2 | 12/2007 | Milliman et al. |
| 7,308,998 B2 | 12/2007 | Mastri et al. |
| 7,311,560 B2 | 12/2007 | Ehr et al. |
| 7,357,287 B2 | 4/2008 | Shelton, IV et al. |
| 7,380,695 B2 | 6/2008 | Doll et al. |
| 7,422,586 B2 | 9/2008 | Morris et al. |
| 7,422,589 B2 | 9/2008 | Newton et al. |
| 7,425,835 B2 | 9/2008 | Eisele |
| 7,452,358 B2 | 11/2008 | Stern et al. |
| 7,465,302 B2 | 12/2008 | Odell et al. |
| 7,473,145 B2 | 1/2009 | Ehr et al. |
| 7,483,738 B2 | 1/2009 | Tamarkin et al. |
| 7,520,877 B2 | 4/2009 | Lee, Jr. et al. |
| 7,566,332 B2 | 7/2009 | Jarrard et al. |
| 7,588,567 B2 | 9/2009 | Beveja et al. |
| 7,637,907 B2 | 12/2009 | Blaha |
| 7,722,412 B2 | 5/2010 | Ehr et al. |
| 7,722,603 B2 | 5/2010 | McPherson |
| 7,736,357 B2 | 6/2010 | Lee, Jr. et al. |
| 7,736,359 B2 | 6/2010 | McPherson |
| 7,771,419 B2 | 8/2010 | Carmel et al. |
| 7,771,422 B2 | 8/2010 | Auge, II et al. |
| 7,837,680 B2 | 11/2010 | Isaacson et al. |
| 7,909,819 B2 | 3/2011 | Falkenstein et al. |
| 7,927,329 B2 | 4/2011 | McPherson |
| 7,938,825 B2 | 5/2011 | Sturm et al. |
| 8,021,360 B2 | 9/2011 | Dunning et al. |
| 8,062,291 B2 | 11/2011 | McPherson |
| 8,080,007 B2 | 12/2011 | Dunning et al. |
| 8,100,898 B2 | 1/2012 | Gregg |
| 2003/0020072 A1 | 1/2003 | Higgins |
| 2003/0139741 A1 | 7/2003 | Goble et al. |
| 2004/0150504 A1 | 8/2004 | Nicholson |
| 2004/0206365 A1 | 10/2004 | Knowlton |
| 2005/0085806 A1 | 4/2005 | Auge, II et al. |
| 2006/0041251 A1 | 2/2006 | Odell et al. |
| 2006/0041252 A1 | 2/2006 | Odell et al. |
| 2006/0079872 A1 | 4/2006 | Eggleston |
| 2006/0173250 A1 | 8/2006 | Nessler |
| 2006/0217742 A1 | 9/2006 | Messerly et al. |
| 2006/0224150 A1 | 10/2006 | Arts et al. |
| 2007/0049914 A1 | 3/2007 | Eggleston |
| 2007/0049916 A1 | 3/2007 | Isaacson et al. |
| 2007/0049919 A1 | 3/2007 | Lee, Jr. et al. |
| 2007/0074719 A1 | 4/2007 | Danek et al. |
| 2007/0161979 A1 | 7/2007 | McPherson |
| 2007/0167942 A1 | 7/2007 | Rick |
| 2007/0203481 A1 | 8/2007 | Gregg et al. |
| 2007/0244478 A1 | 10/2007 | Bahney |
| 2008/0009846 A1 | 1/2008 | Ward |
| 2008/0082092 A1 | 4/2008 | McPherson |
| 2008/0083806 A1 | 4/2008 | Scirica |
| 2008/0083813 A1 | 4/2008 | Zemlok et al. |
| 2008/0097558 A1 | 4/2008 | Eggers et al. |
| 2008/0249520 A1 | 10/2008 | Dunning et al. |
| 2008/0249524 A1 | 10/2008 | Dunning |
| 2008/0281309 A1 | 11/2008 | Dunning et al. |
| 2008/0281310 A1 | 11/2008 | Dunning et al. |
| 2008/0281311 A1 | 11/2008 | Dunning et al. |
| 2009/0036884 A1 | 2/2009 | Gregg et al. |
| 2009/0036885 A1 | 2/2009 | Gregg |
| 2009/0138006 A1 | 5/2009 | Bales et al. |
| 2009/0198229 A1 | 8/2009 | Dunning |
| 2009/0198230 A1 | 8/2009 | Behnke et al. |
| 2009/0209953 A1 | 8/2009 | Schoenman |
| 2009/0223041 A1 | 9/2009 | Garrison et al. |
| 2009/0234352 A1 | 9/2009 | Behnke et al. |
| 2009/0234353 A1 | 9/2009 | McPherson |
| 2010/0185195 A1 | 7/2010 | McPherson |
| 2010/0241023 A1 | 9/2010 | Gilbert |
| 2011/0077641 A1 | 3/2011 | Dunning |
| 2011/0112525 A1 | 5/2011 | Dunning et al. |
| 2011/0112530 A1 | 5/2011 | Keller |
| 2011/0190761 A1 | 8/2011 | McPherson |

FOREIGN PATENT DOCUMENTS

| | | |
|---|---|---|
| DE | 3239640 | 5/1983 |
| DE | 3206947 | 9/1983 |
| DE | 3206947 A1 * | 9/1983 |
| DE | 3544443 | 6/1987 |
| DE | 4238263 | 5/1993 |
| DE | 4231236 | 3/1994 |
| DE | 19717411 | 11/1998 |
| DE | 19751108 | 5/1999 |
| DE | 19801173 | 7/1999 |
| DE | 10328514 | 6/2003 |
| DE | 102004010940 | 9/2005 |
| EP | 0262888 | 4/1988 |
| EP | 390937 | 10/1990 |
| EP | 836868 | 4/1998 |
| EP | 1051949 | 11/2000 |
| EP | 1076350 | 2/2001 |
| EP | 0930048 | 4/2003 |
| EP | 1645236 | 4/2006 |
| EP | 1707151 | 10/2006 |
| EP | 1808144 | 7/2007 |
| EP | 1468653 | 11/2007 |
| EP | 1902684 | 3/2008 |
| EP | 1990020 | 11/2008 |
| EP | 1994905 | 11/2008 |
| EP | 2033588 | 3/2009 |
| FR | 2276027 | 6/1974 |
| FR | 2516782 | 5/1983 |
| GB | 2054382 | 2/1981 |
| GB | 2374532 | 10/2002 |
| WO | WO 93/00862 | 1/1993 |
| WO | WO 96/19152 | 6/1996 |
| WO | WO 97/37719 | 10/1997 |
| WO | WO 98/18395 | 5/1998 |
| WO | WO 98/53751 | 12/1998 |
| WO | WO 99/09899 | 3/1999 |
| WO | WO 99/11187 | 3/1999 |
| WO | WO 00/06246 | 2/2000 |

| | | |
|---|---|---|
| WO | WO 00/32122 | 6/2000 |
| WO | WO 00/53113 | 9/2000 |
| WO | WO 00/65993 | 11/2000 |
| WO | WO 01/87175 | 11/2001 |
| WO | WO 02/024092 | 3/2002 |
| WO | WO 02/058579 | 8/2002 |
| WO | WO 02/060526 | 8/2002 |
| WO | WO 02/099442 | 12/2002 |
| WO | WO 03/094766 | 11/2003 |
| WO | WO 2004/028385 | 4/2004 |
| WO | WO 2004/074854 | 9/2004 |
| WO | WO 2005/048809 | 6/2005 |
| WO | WO 2005/087124 | 9/2005 |
| WO | WO 2005087124 A1 * | 9/2005 |
| WO | WO 2005/099606 | 10/2005 |
| WO | WO 2005/110263 | 11/2005 |
| WO | WO 2005/115262 | 12/2005 |
| WO | WO 2008/009385 | 1/2008 |
| WO | WO 2009/031995 | 3/2009 |
| WO | WO 2009/099960 | 8/2009 |

OTHER PUBLICATIONS

U.S. Appl. No. 11/900,190, filed Sep. 10, 2007, Jeffrey L. Eggleston.
U.S. Appl. No. 13/326,040, filed Dec. 14, 2011, Dunning et al.
U.S. Appl. No. 13/343,181, filed Jan. 4, 2012, William N. Gregg.
Boyles, Walt; "Instrumentation Reference Book", 2002; Butterworth-Heinemann; 262-264.
International Search Report EP05002027.0 dated May 12, 2005.
International Search Report EP05021944.3 dated Jan. 25, 2006.
International Search Report EP06006961 dated Aug. 3, 2006.
International Search Report EP06006961.4 dated Oct. 5, 2007.
International Search Report -extended EP06008198.1 dated Jun. 18, 2010.
International Search Report EP06018206.0 dated Oct. 13, 2006.
International Search Report EP06023756.7 dated Feb. 21, 2008.
International Search Report EP07000567.3 dated Dec. 3, 2008.
International Search Report EP07000885.9 dated May 15, 2007.
International Search Report EP07007783.9 dated Aug. 6, 2007.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09003809.2 dated Jun. 29, 2009.
International Search Report EP09003813.4 dated Aug. 3, 2009.
International Search Report EP09152032 dated Jun. 17, 2009.
International Search Report EP09152130.2 dated Apr. 6, 2009.
International Search Report EP09152899.2 dated Jul. 1, 2009.
International Search Report EP10157054.7 dated Sep. 9, 2010.
International Search Report EP10190322.7 dated Feb. 18, 2011.
International Search Report PCT/US2004/004196 dated Oct. 4, 2007.

* cited by examiner

ELECTROSURGICAL SYSTEM FOR MEASURING CONTACT QUALITY OF A RETURN PAD

CROSS-REFERENCE TO RELATED APPLICATION

This application is a Divisional of U.S. patent application Ser. No. 11/800,687, filed May 7, 2007, now U.S. Pat. No. 8,080,007, the entirety of which is incorporated by reference herein for all purposes.

BACKGROUND

1. Technical Field

The present disclosure relates to an electrosurgical return pad, and more particularly, the present disclosure relates to an electrosurgical return pad with contact quality monitoring for use during electrosurgery.

2. Background of Related Art

Electrosurgery is the application of electricity and/or electromagnetic waves to cut or modify biological tissue during a surgical procedure. Generally, electrosurgery utilizes an electrosurgical generator, a return electrode, and a source electrode. The electrosurgical generator produces an electromagnetic wave, typically above 100 kilohertz, between the return and source electrodes when applied to tissue. The electromagnetic wave created therebetween dissipates energy as heat as it travels from one electrode to the other. Electromagnetic frequencies above 100 kilohertz are employed to avoid muscle and/or nerve stimulation.

During electrosurgery, current generated by the electrosurgical generator is conducted through patient tissue between the two electrodes. The current causes the tissue to heat up as the electromagnetic waves overcome the tissue impedance. Although, many other variables affect the total heating of the tissue, usually with more current density, increased heating results. Current can be used for cutting, dissection, ablation, arresting blood loss and coagulation, and are well-known.

The two basic types of electrosurgery employed are monopolar and bipolar electrosurgery. Both types use an "active" and a "return" electrode, although the distinction is not always necessary. In bipolar electrosurgery, the surgical instrument has an active electrode and a return electrode on the same instrument or in very close proximity, usually causing current to flow through a smaller amount of tissue. In monopolar electrosurgery, the return electrode is located elsewhere on the patient's body and is usually not part of the surgical instrument itself. In monopolar electrosurgery, the return electrode is part of a device referred herein as a return pad.

The return pad is intended to lower the current density in nearby tissue when current flows between the return pad and the patient's tissue. The current density through the tissue near the return pad is related to the impedance between the tissue and the return pad. This impedance is referred to herein as contact impedance. When the surface area of the return electrode contacting the skin is reduced, increases in current density may heat tissue up to the point of possibly causing skin damage. Maintaining low contact impedance helps prevent electrosurgery related injuries.

Generally, resistive electrodes tend to have more uneven heating than capacitive electrodes. Because electricity tends to conduct through the path of least resistance, more current tends to conduct through the tissue near the edge of a resistive electrode that is closest to the active electrode, creating more localized heat. This is known as the "edge effect". Although, capacitive electrodes tend to have more uniform heating than resistive electrodes, measuring contact quality has been more difficult.

SUMMARY

The present disclosure relates to an electrosurgical return pad, and more particularly, the present disclosure relates to an electrosurgical return pad with contact quality monitoring for use during electrosurgery.

In one embodiment, the return pad includes a backing, at least one return electrode, and at least one ring sensor. The backing has a top side, a bottom side, and a periphery. The return electrode is disposed on the bottom side of the backing layer and is adapted to connect to a current generator. The return electrode may be capacitive or resistive; and the ring sensor may be capacitive or resistive. The ring sensor may be disposed in substantial concentric registration with the periphery of the backing. Additionally or alternatively, the ring sensor may be disposed in substantial vertical registry with the bottom side of the backing layer. The ring sensor may also be configured to connect to a measuring component. The measuring component is operable to approximate contact quality of the return electrode during electrosurgical application and may be configured to communicate with the generator.

In another embodiment, the ring sensor may include two partially concentric ring electrodes configured to cooperate with the measuring component. The ring sensor can measure contact quality during an electro surgical procedure and communicate contact quality to the generator. The two ring electrodes may be disposed in substantial vertical registry with the return electrode.

In yet another embodiment, a patient interface material may be disposed between the backing layer of the return pad and skin. The patient interface material may also be configured to facilitate contact quality monitoring of the return electrode. The interface material may include a conductive gel, a conductive adhesive, an insulating gel, an insulating adhesive, a dielectric gel, a dielectric adhesive, an insulator, and/or some combination thereof. The ring sensor may include a temperature sensitive material that may be configured to sense contact quality based upon temperature, e.g., a positive temperature coefficient ink.

In another embodiment a control component of the generator may be utilized; and the measuring component may be configured to receive and process sensor data and relay the sensor data to the control component. The return electrode may be configured to electrically isolate the return electrode from the generator when the measurement component determines that a threshold condition has been reached. Additionally or alternatively, the return pad may include an intelligence component that may be configured to process sensor data and analyze the data with a risk function algorithm.

In yet another embodiment, a method for monitoring contact quality of a return pad described above is disclosed. The method includes the steps of: providing a return pad; activating at least one ring sensor of the return pad to operatively communicate with a measuring component; and approximating the contact quality of the return electrode by analyzing capacitance, impedance and/or resistance from the at least one ring sensor. The methodology may further include the step of electrically isolating the return electrode of the return pad from a generator when the measuring component determines that a threshold condition has been reached.

In another embodiment, an electrosurgical system for measuring contact quality of a return pad is discussed. The system includes a return pad, a return interface and a sensing interface. The return pad includes a backing layer, a first capacitive electrode and a second capacitive electrode. The first and second electrodes may be disposed on the backing layer. The return interface may be adapted to return current for the first and second capacitive electrodes. The sensing interface may be operatively coupled to a generator and configured to monitor the impedance between the first and second capacitive electrodes to determine contact quality. Additionally or alternatively, the sensing interface is operatively coupled to a generator and is configured to monitor a return current difference between the first and second capacitive electrodes to determine contact quality.

BRIEF DESCRIPTION OF THE DRAWINGS

Various embodiments of the subject instrument are described herein with reference to the drawings wherein.

DETAILED DESCRIPTION

Figure 1A:
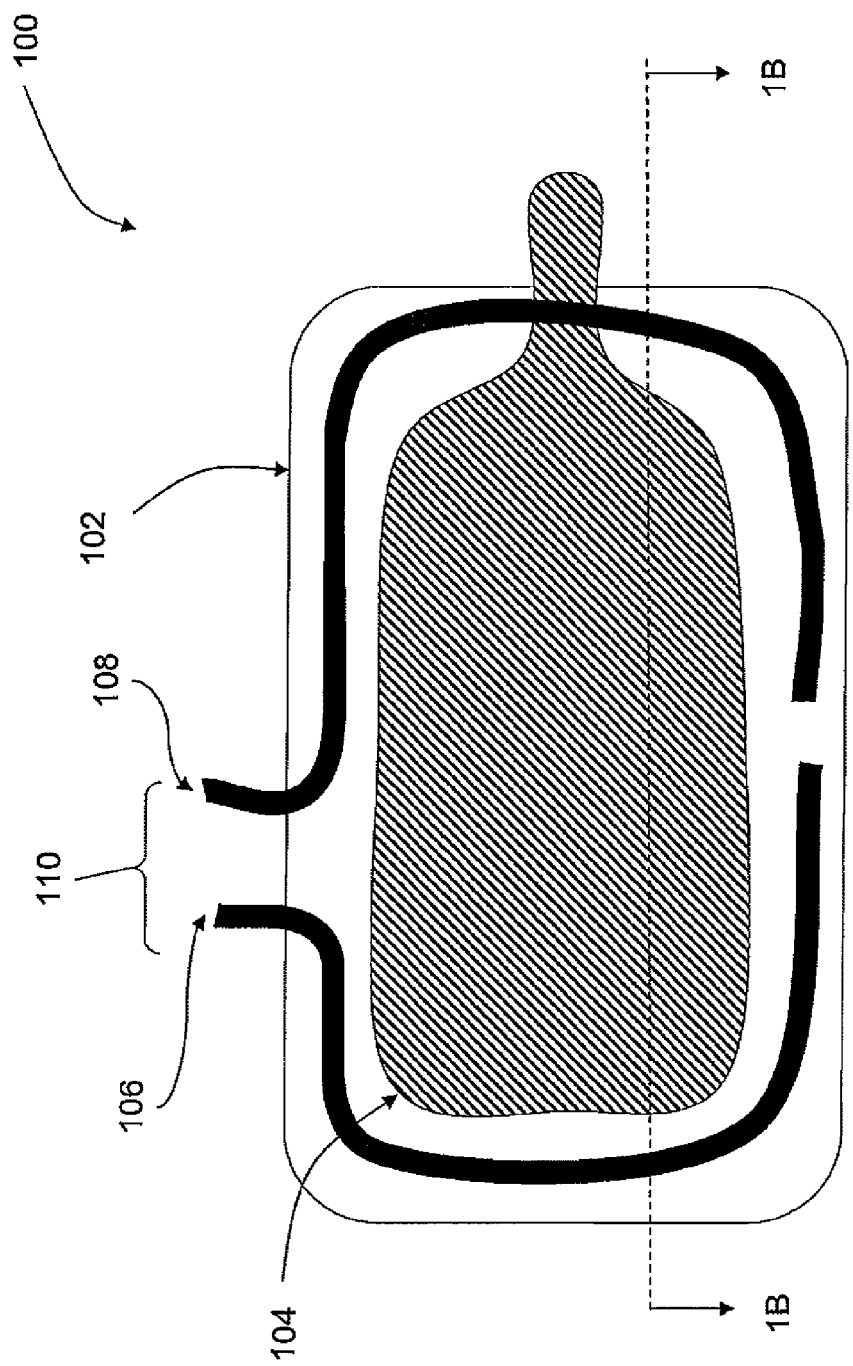
FIG. 1A is a schematic bottom-view of a return pad according to one embodiment of the present disclosure showing two ring electrodes disposed in substantial concentric registration with the periphery of the backing.

The embodiments that follow are described with reference to the attached drawings. Like reference numerals are used to refer to like elements, steps or features but are not intended to indicate identical features. The word "component" is used herein to refer to an entity that relates to and/or utilizes hardware, software, circuitry, transducers, a microprocessor, a microcontroller, software in execution, or some combination thereof. The term "impedance" is not intended to limit, but rather is to describe the natural phenomenon of a material's opposition to a wave as the wave propagates through the material, where the type of waves included are electromagnetic waves, electrical waves, electricity waves, RF waves, AM-frequency waves, FM-frequency waves, microwave waves, or any other wave of oscillating electrical charge or magnetic field. In addition, the term "current" is used herein to describe the flow of electrical charge.

Turning to FIGS. 1A-5, several embodiments of the present disclosure are shown that utilize a ring sensor. FIGS. 1A-4 are schematic views of a return pad that includes a ring sensor having two electrodes while FIGS. 5A and 5B show a ring sensor that has one electrode.

Referring initially to FIG. 1A, a return pad 100 is shown that includes a backing 102 (FIG. 1A-5) that supports a return electrode 104 (FIGS. 1A-5). Backing 102 has a ring sensor 110 disposed in substantial concentric registration with the periphery of backing 102 as shown by FIGS. 1A-5A with two electrodes 106 and 108 or may have a ring sensor 508 with one electrode 506.

The backing 102 may be made of cloth, cardboard or any other material to facilitate return pad operation. The return electrode 104 may be made from materials that include aluminum, copper, mylar, metalized mylar or other suitable conductive material. Electrode 104 may also include an insulator, glue, adhesive, gel or other material that is configured to attach the return electrode 104 to tissue. Return electrode 104 may additionally include a dielectric, insulator or other material positioned between a conductor and tissue to enhance capacitive properties of the return electrode as explained in more detail below.

Figure 4:
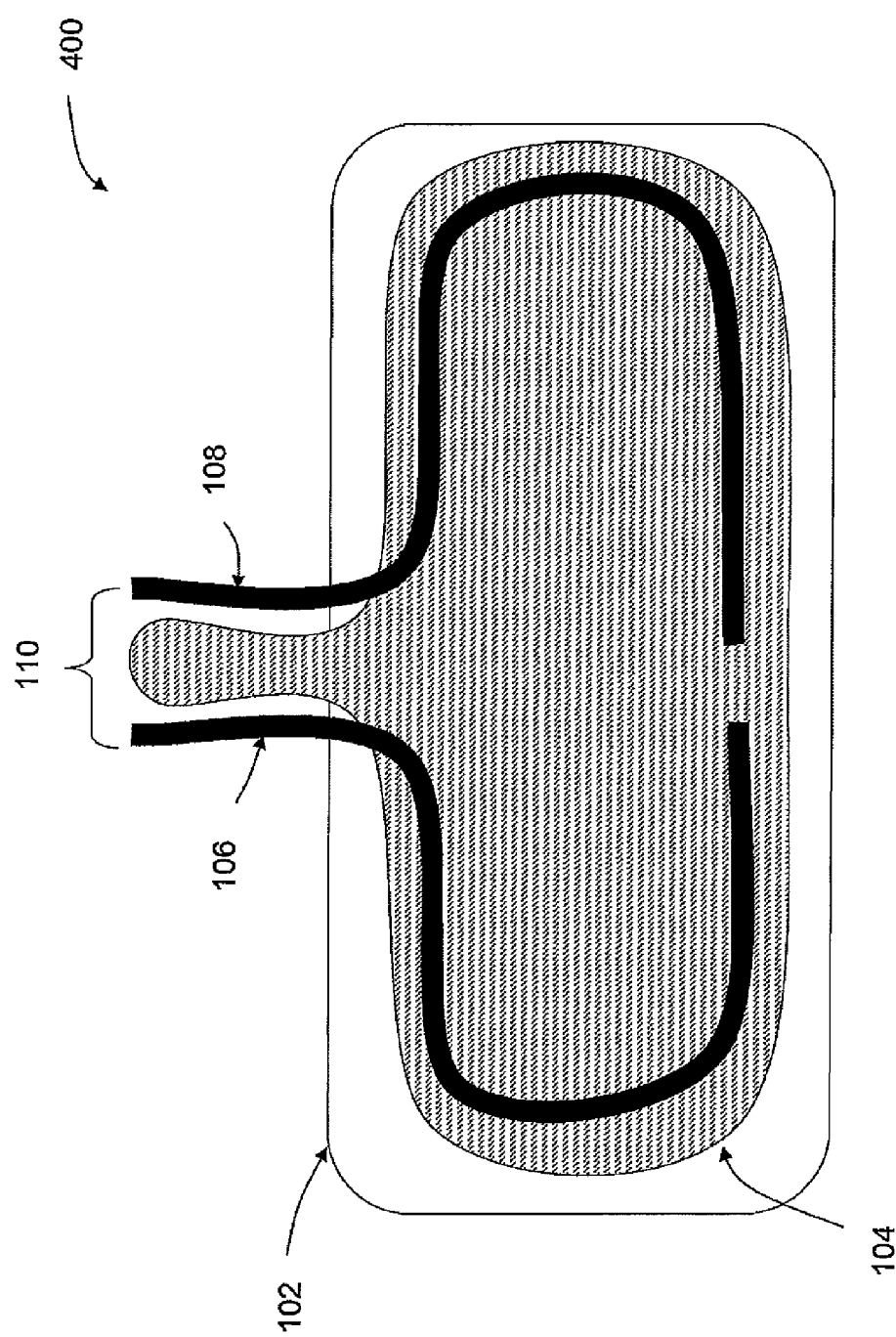
FIG. 4 is a schematic bottom view showing a return pad having a ring sensor in substantial vertical registry with the return electrode in accordance with the present disclosure.
Figure 5A:
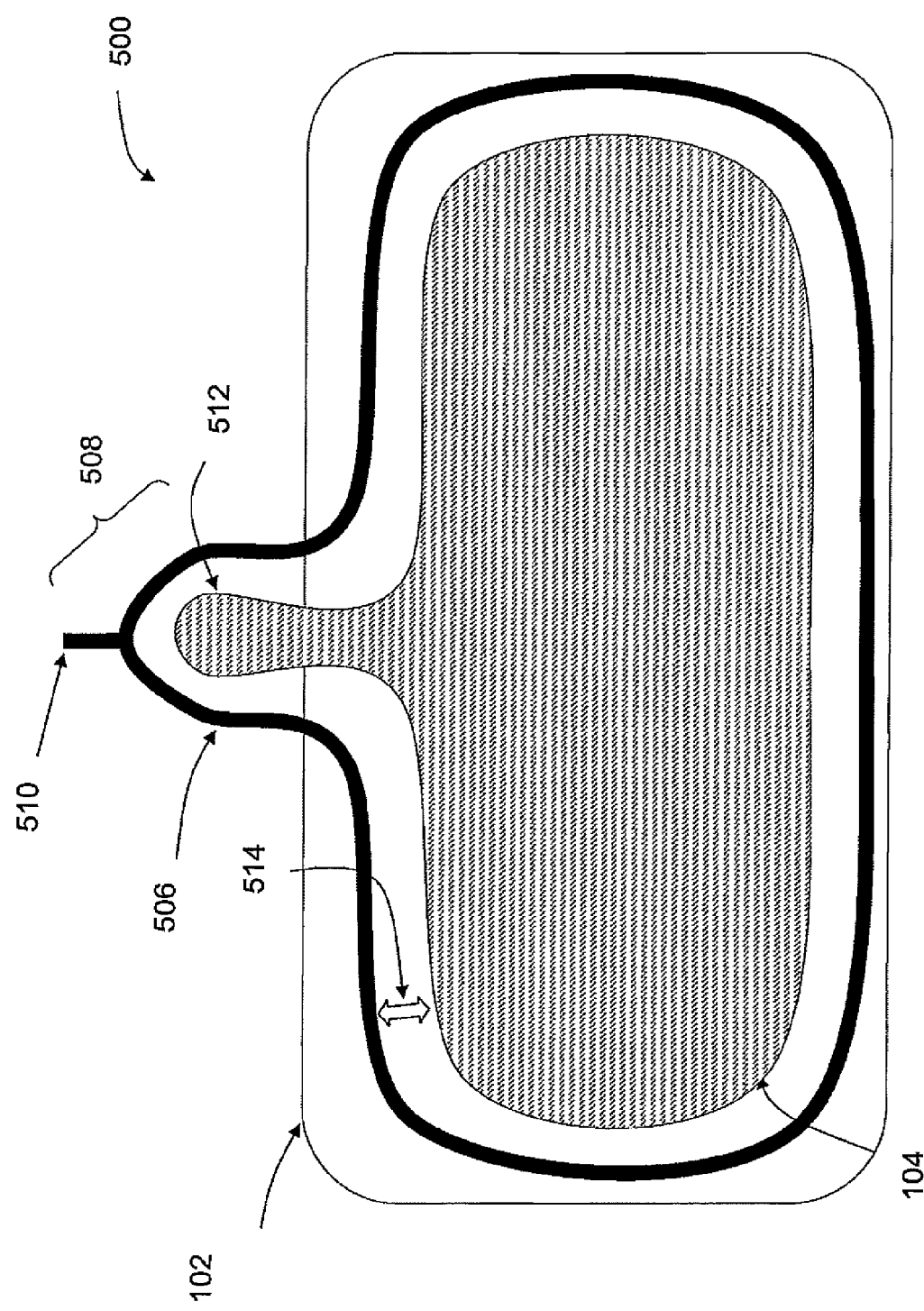
FIG. 5A is a schematic bottom view showing a return pad that utilizes a ring sensor with a single ring electrode in accordance with the present disclosure.

As mentioned above, ring electrodes 106 and 108 form ring sensor 110 (FIGS. 1A-5) while ring electrode 506 forms ring sensor 508 (FIG. 5A). The term "ring" is not meant to define a circle, arc, or other shape, but is intended to indicate any shape possible to measure the impedance of a given contact area of a return pad 100, 200, 300, 400 or 500. Ring sensor 110 or 508 may also include an insulator, glue, adhesive, gel or other suitable material to attach return electrode 104 to either backing 102 and/or to tissue. Additionally ring sensor 110 may be electrically isolated from return electrode 104.

One example of use of a return pad 100 according to the present disclosure includes a return electrode 104 in a capacitive configuration with ring sensor 110 in a resistive configuration. In this example, RF energy can return through 104 while concurrently having an oscillating current between ring electrode 106 and ring electrode 108 to produce a current through contacting tissue approximately below return electrode 104. If the center portion of return pad 100 starts tenting (i.e., starts peeling away from the skin), the impedance measurement from ring electrode 106 and ring electrode 108 may increase. If a rise in impedance is significant enough, generator 516 (see FIG. 7) measures this change in impedance and may trigger an event, e.g., an alarm, a warning, and/or may prevent any therapeutic current from flowing until a safe impedance level exists.

Figure 1B:
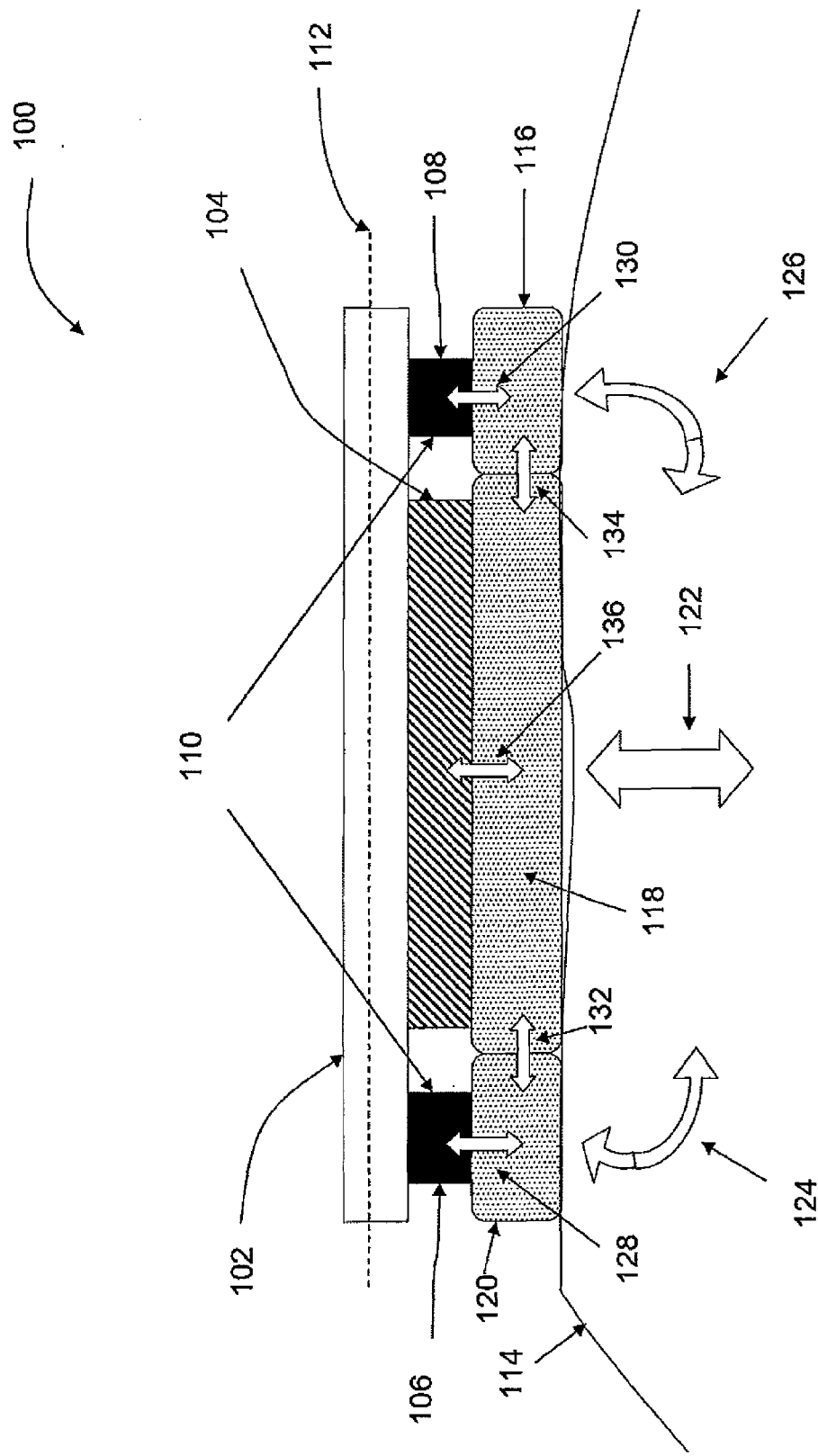
FIG. 1B is a schematic cross sectional view along line 1B-1B of the return pad of FIG. 1A.

Turning now to the more detailed depiction of a return pad 100 in use, FIG. 1B is a cross section view of return pad 100, along axis 1B-1B, contacting skin barrier 114. Return pad 100 also includes an interface material 116 disposed between ring electrode 108 and skin barrier 114, an interface material 118 disposed between return electrode 104 and skin barrier 114, and an interface material 120 disposed between ring electrode 106 and skin barrier 114.

Current arrows 122 depict current traveling through the skin barrier 114 and interface material 118. Current arrows 124 depict current traveling through the skin barrier 114 and interface material 120; and current arrows 126 depict current traveling through the skin barrier 114 and interface material 116. Current arrows 128 and 130 depict current traveling between ring electrodes 106, 108 and interface materials 120, 116, respectively. Current arrows 132, 134 depict current traveling between interface materials 120, 116, and 118 and current arrows 136 depict current which may travel between return electrode 104 and interface material 118.

Interface materials 118, 120, or 116 may be conductive, insulating, dielectric, or can have any other electrical property. Additionally or alternatively, interface material 118, 120, or 116 may provide adhesion or temperature dependent properties. In another embodiment, there may be electrical insulation (including air) between interface material 118 and 116 and/or between interface material 118 and 120 (not shown in this configuration). Adding insulation and/or an air gap between interface materials 118 and 116, and/or between interface materials 118 and 120 to reduced current arrows 134 and 132, respectively, may increase the sensitivity of ring sensor 110.

A measuring component 706 (FIG. 7), may be operatively coupled to ring sensor 110 to measure the various impedances of the return pad 120. These impedance measurements may be conducted utilizing current in various ways. For example, by changing frequency, voltage, wattage, or amperage one skilled in the art can make an approximate impedance measurement. Applying a voltage differential across ring electrode 106 and ring electrode 108 will produce current 130 and current 128. Current 128 can either flow through skin 114 to produce current 124, or through interface material 118 to produce current 132. In addition, current 130 can flow either through skin 114 to produce current 126 or to interface material 118 to produce current 134. If return pad 100 starts to have a reduced contact with skin 114, current 124 and current 126 will change based upon changing impedance. A change of impedance thus reflects a change in return pad contact with tissue 114.

One way to effectively approximate impedance is to assume that impedance $Z_0$ is defined as the impedance from ring electrode 106, through interface material 120, through interface material 118, through interface material 116 and to ring electrode 108. Also, assume that impedance $Z_1$ is defined as the impedance from interface material 120 through skin 114 and then through interface material 116. In this case, the total impedance, $Z_{total}$ measured by ring sensor 110 is approximately the impedance of $Z_0$ in parallel with $Z_1$. Thus, the relationship is described as $Z_{total} \approx Z_0 \| Z_1$. Any change of contact impedance from interface material 120 and skin 114 or interface material 116 and skin 114 would thus have an impact of $Z_{total}$ and is measurable. By utilizing various conductive and insulating materials, it is possible to keep impedances approximately constant (in this example, $Z_0$) so that the impedance being measured (in this example $Z_1$) can be more accurately ascertained.

Measuring component 706 (see FIG. 7) may be configured to take into account current produced by return electrode 104 and that suitable signal conditioning can be employed to account for this current. Also, ring electrode 106 and ring electrode 108 may employ the use of a temperature dependent material so that changes in temperature are reflected in an impedance measurement.

Figure 2:
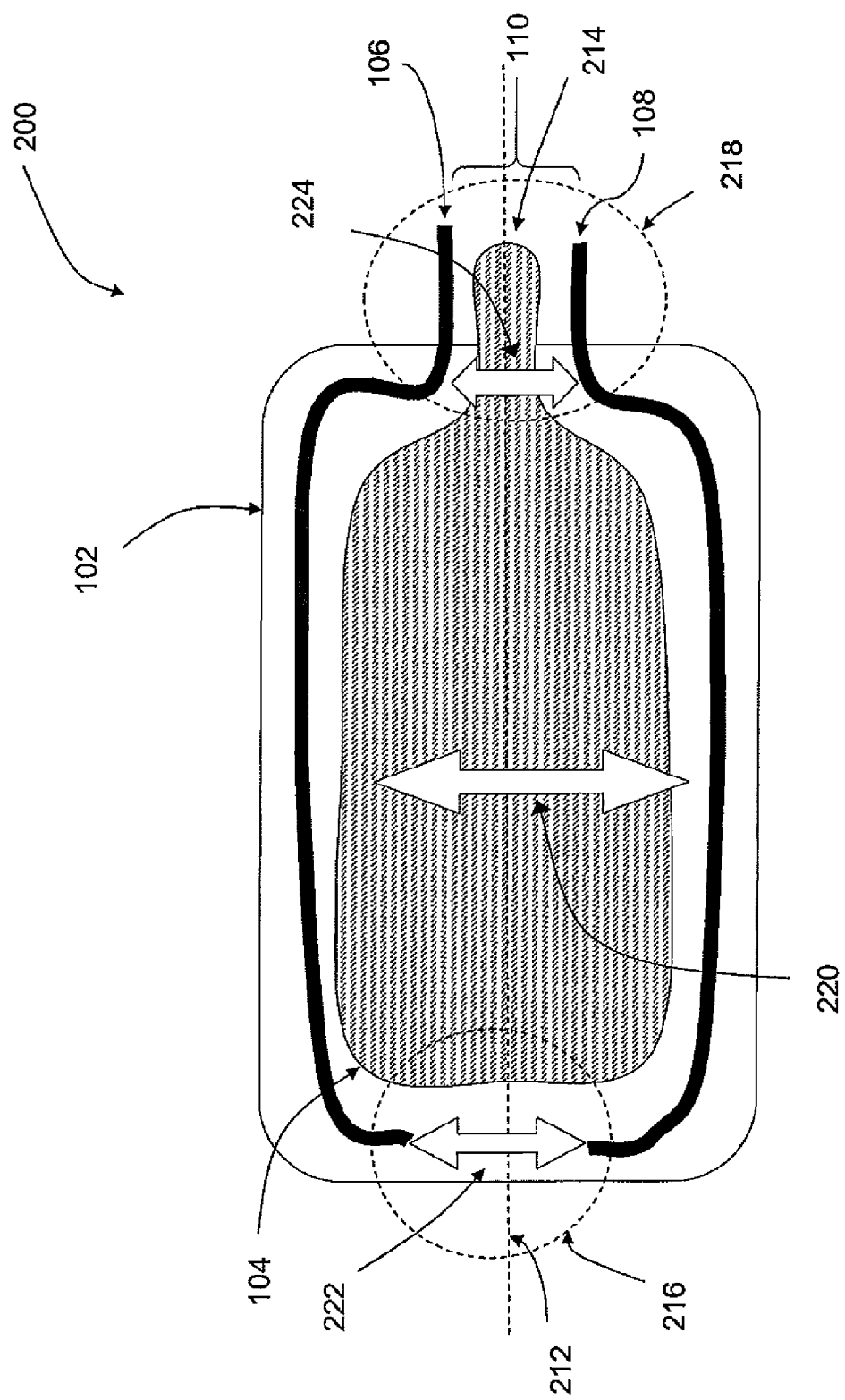
FIG. 2 is a schematic bottom view of another embodiment of the present disclosure showing a return pad having a ring sensor with a distal end having a break point in accordance with the present disclosure.

As shown in FIGS. 1A and 2, the area between ring electrode 106 and ring electrode 108 is configured to approximate the contacting area of the pad 100 to skin 114. Contrast this to FIG. 3A that has electrodes 106 and 108 configured to measure contact quality near the periphery of return electrode 104. The general shape of ring sensor 110 may vary in order to effectively measure the contact quality of various portions of a return pad.

Turning now to another ring sensor 110 configuration of the present disclosure, FIG. 2 depicts a return pad 200 having a backing 102 with a return electrode 104. Return electrode 104 may be in a resistive configuration or in a capacitive configuration. A first ring electrode 106 and a second ring electrode 108 form ring sensor 110. Ring sensor 110 may be capacitive or resistive. Ring sensor 110 is disposed in substantial concentric registration with the periphery of backing 102. Current (not shown) exits return pad 200 via connector region 214. Break point 216, depicted as a dashed-lined oval, is the general region where ring electrode 106 and ring electrode 108, if connected, would have made ring sensor 110 a single electrode. Ring return region 218, also depicted as a dashed-line oval, is the general area where the ring sensor 110 signal exits return pad 200. A ring sensor reading may be taken from ring return region 218 either directly or indirectly with the aide of an electrical conductor and/or waveguide for further analysis (see FIG. 7, waveguide 716). The term waveguide includes but is not limited to: a coaxial cable, a conductor, a plurality of conductors, an insulator, a dielectric, shielding, cabling, connectors, or some combination thereof.

Electrical current is depicted in FIG. 2 as if the pad were contacting tissue or if a conductive material were present. Current arrow 220 is a representation of the majority of the current flowing between ring electrode 106 and ring electrode 108. Current arrow 222 depicts current flowing from ring electrode 108 and ring electrode 106 near break point 216 and current arrow 224 depicts current flowing from electrode 108 and ring electrode 106 near exit point 218.

A measuring component 706 (see FIG. 7), can produce a current utilizing ring sensor 110 to measure impedance. As the return pad contacts tissue barrier 114, currents 220, 222, and 224 can change based upon return pad 200's contact with tissue barrier 114. Respective changes in currents 220, 222, and 224 may be dependant upon geometry, interface material and other variables. For example, measured impedance may be more responsive to changes in contact impedance around break point 216. Thus it may be advantageous to change the geometry, material used, or thickness of ring electrode 106 or ring electrode 108 near break point 216 to accommodate for this abnormality. It may be advantageous in certain circumstances to configure certain portions of the ring electrode to have increased or reduced areas of sensitivity depending upon a particular purpose. An interface material (not shown in FIG. 2 with return pad 200) may be included to modify ring sensor's 110 signal or the return current throughout return pad 200 and/or may aide in securing return pad 200 to tissue and/or skin.

Although return pad 200 is depicted as having a connector region 214 near ring return region 218, the connector region 214 may not be located on the same portion or near each other on return pad 200, i.e., the ring sensor signal may exit from any location on or near return pad 200. Additionally or alternatively, the return signal may exit return pad 200 from any location as well depending on a particular pad 200 configuration. Break point 216 may also be located at any position on return pad 200.

Figure 3A:
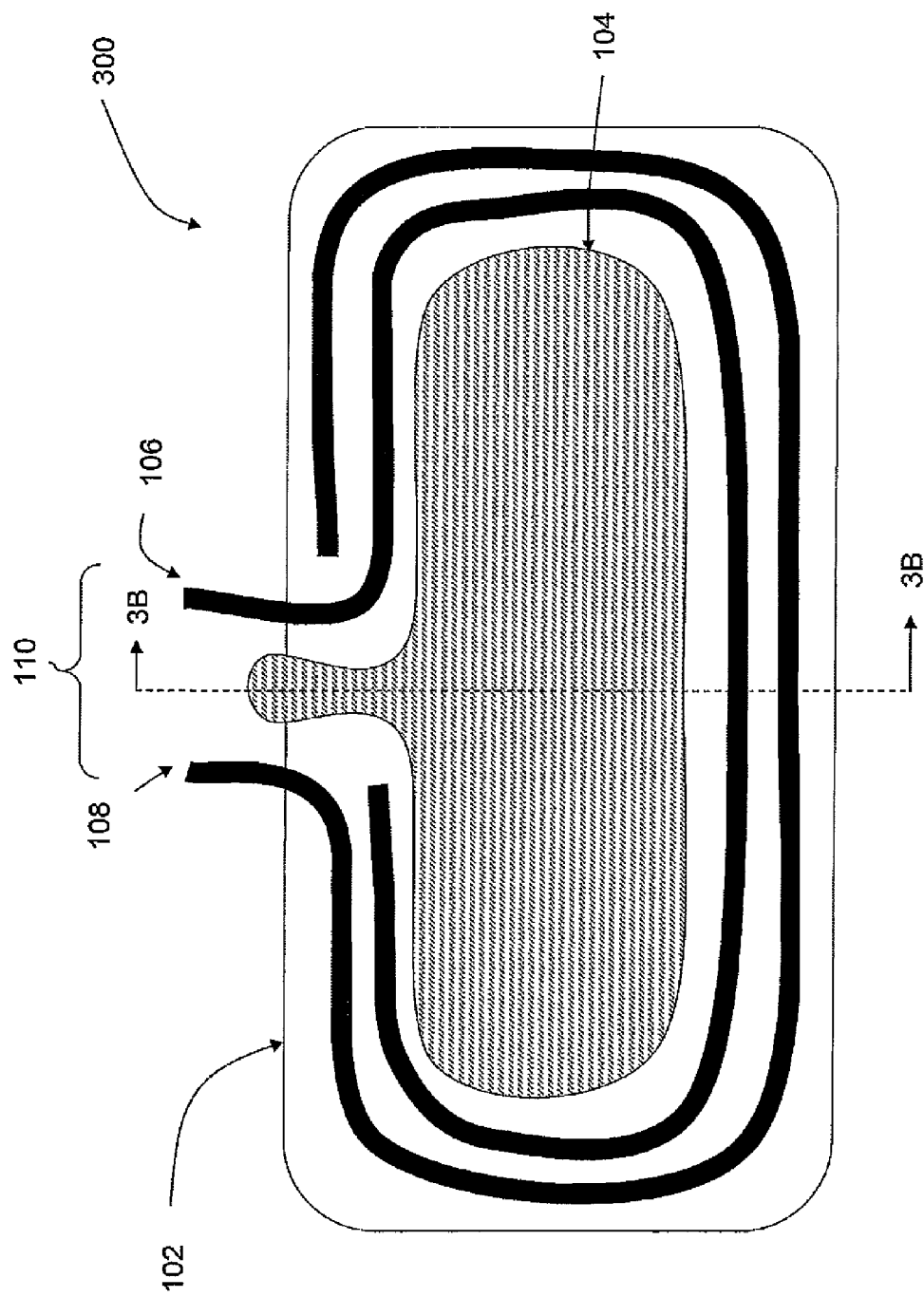
FIG. 3A is a schematic bottom view showing a return pad having two concentrically aligned ring electrodes in accordance with the present disclosure.
Figure 3B:
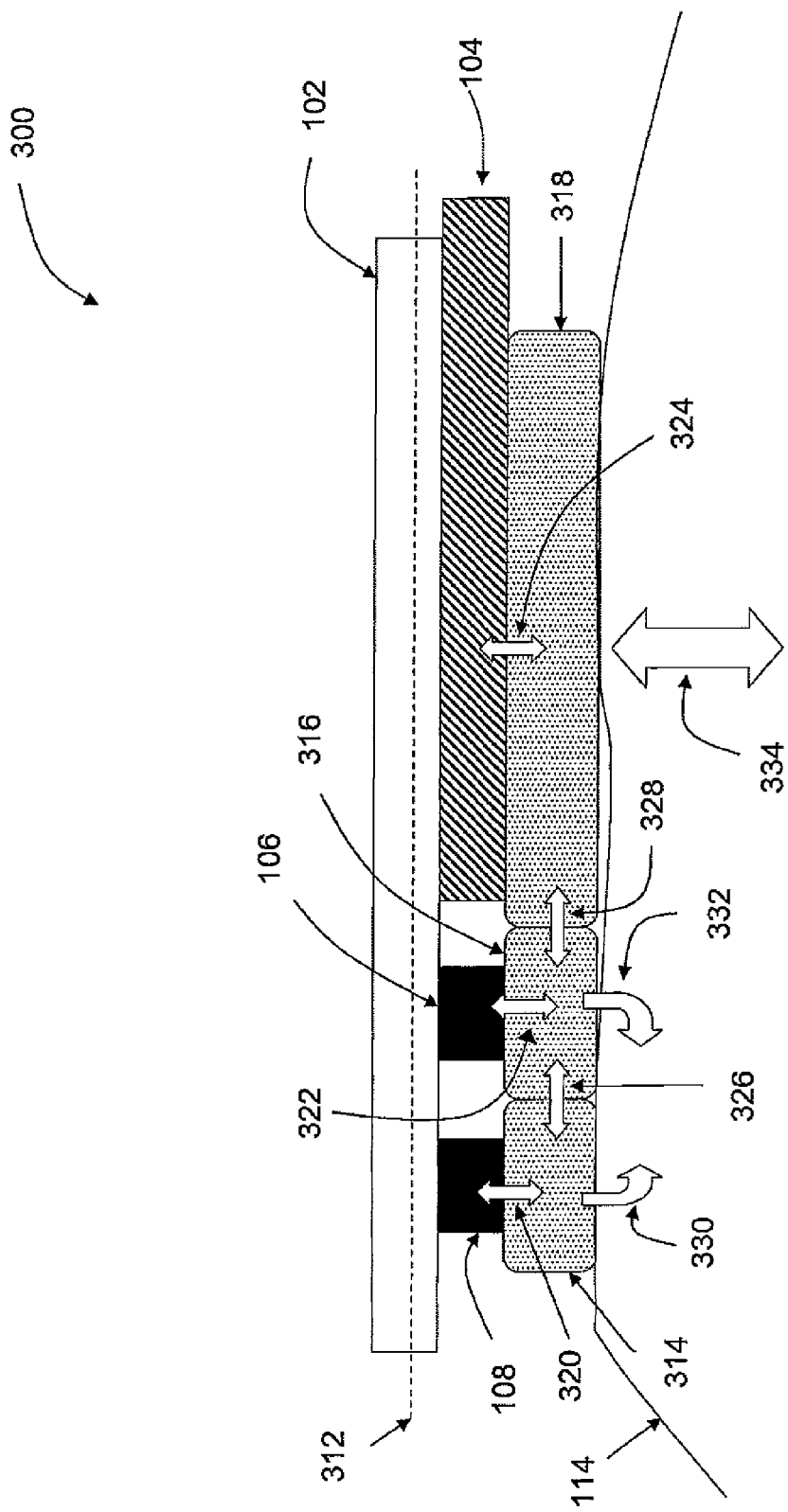
FIG. 3B is a schematic cross sectional view along line 3B-3B of the return pad of FIG. 3A.

FIGS. 3A and 3B show another embodiment of the present disclosure having a return pad 300 that facilitates peeling detection and has a ring sensor 110 in a different configuration than in FIGS. 1A-2. Return pad 300 includes a backing 102 made of any material as described above that provides support for return pad 300. Ring electrode 106 and ring electrode 108 again are configured to form ring sensor 110. And ring sensor 110 may be capacitive or resistive.

Ring electrode 106 and ring electrode 108 are disposed in substantial concentric registration with the periphery of backing 102. Electrode 104 is disposed relative to ring electrode 106 and 108 in a generally concentric fashion, which is configured to facilitate peel detection. The impedance measurement taken from ring sensor 110 is primarily a function of contact impedance between ring electrode 106 and ring electrode 108. Any edge peeling would affect the measured impedance thus allowing measuring component 706 (see FIG. 7) to measure this effect.

FIG. 3B shows a cross sectional view of FIG. 3A along line 3B-3B. Ring electrodes 108, 106 and return electrode 104 interface with skin barrier 114 through interface material 314, 316 and 318, respectively. Current arrows 320 depict current crossing the barrier between ring electrode 108 and interface material 314. Current arrows 322 depict current that crosses the return electrode 106 and the interface material 316 barrier, and current arrows 324 depict the current that crosses the return electrode 104 and interface material 318 barrier. Current arrows 326 depict current crossing the barrier of interface material 314 and 316, and current arrows 328 depict current crossing the barrier of interface material 316 and 318. Interface material 314/skin barrier 114, interface material 316/skin barrier 114, and interface material 318/skin barrier 114 show current arrows as 330, 332 and 334, respectively. Interface materials 314, 316, and 318 are not necessary or critical and may either be an adhesive or gel and may be either insulating or conductive. In yet another configuration, there may be an insulator (including air) between interface materials 314 and 316 (not shown) causing current (represented by arrows 326) to be reduced. The reduction (or elimination) of current represented by current arrows 326 may increase the sensitivity of ring sensor 110.

Return pad 300 is shown as contacting skin barrier 114 and illustrates the effects that an edge peel would have on an impedance measurement in this configuration. To measure impedance, a DC or AC signal may be applied across ring electrode 108 and ring electrode 106 to produce a current. An analysis of the current 320 and/or 322 can be the basis for monitoring contact quality. For example, if interface material 314 partially peeled away from skin 114, then the impedance across the 314 interface material/skin barrier 114 would increase and a larger voltage would be necessary to maintain the previous current levels of current 320 and/or current 322. This increase in voltage would correspond to an increase in contact impedance, which would be recognized by the electrosurgical unit 702.

FIG. 4 shows another embodiment of the present disclosure having a return pad 400 that also facilitates peeling detection and has a ring sensor 110 in a different configuration than in FIGS. 1A-3B. Return pad 400 includes a backing 102 made of any material as described above that provides support for return pad 400. Ring electrode 106 and ring electrode 108 are configured to form ring sensor 110. Ring sensor 110 may be capacitive or resistive.

In contrast to FIGS. 3A-3B, the FIG. 4 ring electrode 106 and ring electrode 108 are disposed in substantial vertical registry with the return electrode 104. Electrode 104 is disposed relative to ring electrode 106 and 108 in a generally concentric fashion, which is also configured to enhance peel detection. The impedance measurement taken from ring sensor 110 is primarily a function of contact impedance between ring electrode 106 and ring electrode 108. Any edge peeling would affect the measured impedance thus allowing measuring component 706 (see FIG. 7) to measure this effect.

To avoid an electrical contact between return electrode 104, and ring electrodes 106 and 108, an electrical insulator (not shown) may be positioned therebetween to avoid any unwanted electrical connections. Any suitable insulator may be used.

Although FIGS. 1A-4 have a ring sensor 110 with ring electrodes 106 and 108, FIG. 5A shows another embodiment according to the present disclosure which utilizes a single ring electrode 506 in ring sensor 508. Return pad 500 includes a backing 102 and a return electrode 104 that, as previously mentioned, may be in a capacitive or a resistive configuration. A ring sensor 508 is located approximately near the periphery of return electrode 104 and is shown as a single ring electrode 506. Sensor interface 510 is depicted and is configured to interface with measuring component 706 (see FIG. 7). Return electrode 104 also has a return interface 512 and is configured to attached to the generator 702 (see FIG. 7).

A small arrow representing current is shown as current arrows 514. Although not all current is shown, the region between the outer edge of return electrode 104 and ring sensor 508 can have current flowing therebetween when contacting tissue. Measuring the impedance between return electrode 104 and ring sensor 508 can be accomplished with a control circuit by utilizing a common reference, e.g., a ground. One example of a control circuit is shown in 5B.

By changing the behavior of current traveling between return electrode 104 and ring sensor 508 impedance can be measured that relates predominately to the contact impedance of return electrode 104 and ring sensor 508. Any reduction in skin contact of the edges around or near return electrode 504 would result in an increase of measured impedance.

As mentioned above, FIG. 5B is a block diagram of a system 514 illustrating the impedances associated with return pad 500 when applied to a patient. Return pad 500 includes ring sensor 508 and return electrode 504. Current generator 516 is shown and provides energy. Patient 520 is depicted as a dashed-line block, and measuring component 522 is shown and connects to patient 520 via ring sensor 508. Measuring component 522 may be separate and distinct to current generator 516. Additionally or alternatively, measuring component 522 may be part of current generator 516. Primary body impedance 530 is a representation of the impedance between surgical instrument 518 and return electrode 504 including the contact impedances of return electrode 504 and surgical instrument 518. Secondary body impedance 526 is the representation of the impedance between ring sensor 508 and return electrode 504 including the contact impedances of ring sensor 508 and return electrode 512. Measuring component 522 and current generator 516 may be referenced to the same ground 532.

In use, if return pad 500 started to peel off of a patient, the contact impedance of ring electrode 506 would increase also increasing the contact impedance of ring sensor 508; thus, measuring component 522 would measure an increase in impedance of secondary body impedance 526 because that includes the contact impedance of ring sensor 508. Since impedance measured by measuring component 522 is the addition of the impedances of ring sensor 508, secondary body impedance 526, and return electrode 504, measuring component 522 will sense any change in secondary body impedance 526 which includes the contact impedances of return electrode 504 and ring sensor 508. E.g., if return electrode 504 starts "tenting", measuring component 522 will also detect a rise in contact impedance of ring sensor 508 as a rise in secondary body impedance 526 and communicate with the generator to compensate for the abnormality.

Measuring component 522 measures contact quality by measuring impedance. For example, measuring component 522 may utilize ring sensor 110 (see FIGS. 1A-4) in one embodiment or ring sensor 508 (see FIG. 5A) in another embodiment to create a test signal that conducts through a patient and/or other return pad material to measuring the contact quality. Measuring component 522 may change the frequency, voltage, wattage, amperage, and/or modulation to accomplish a measurement or may keep any of the aforementioned properties of the signal constant. Additionally, measuring component 522 may monitor any of the aforementioned signal aspects to estimate contact quality. For example, measuring component 522 may keep the voltage of a signal constant and may measure any changes in current to estimate contact quality. The relationships between voltage, current, and impedance are well known.

Figure 5B:
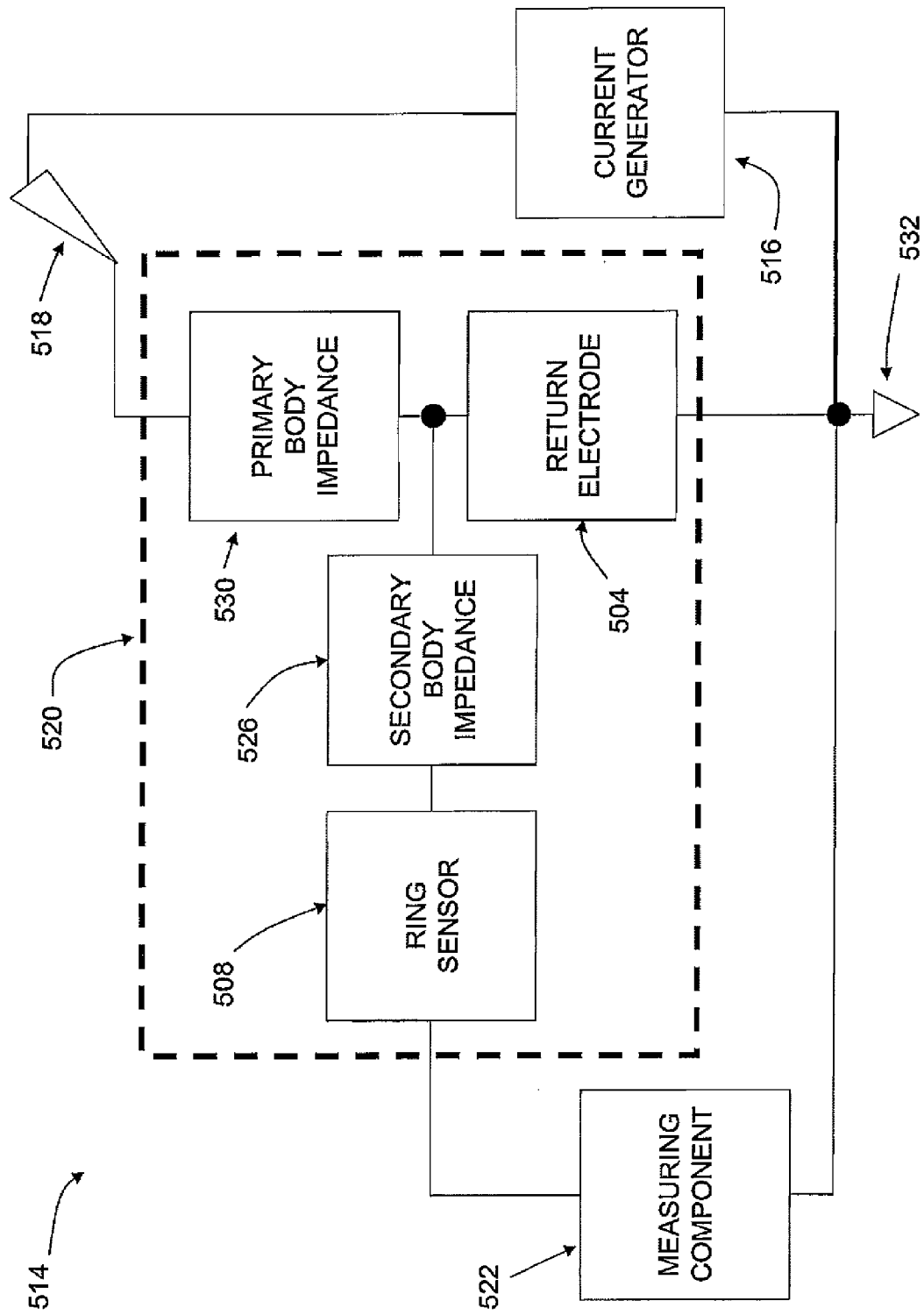
FIG. 5B is a block diagram illustration of the impedances associated with the return pad of FIG. 5A.
Figure 6A:
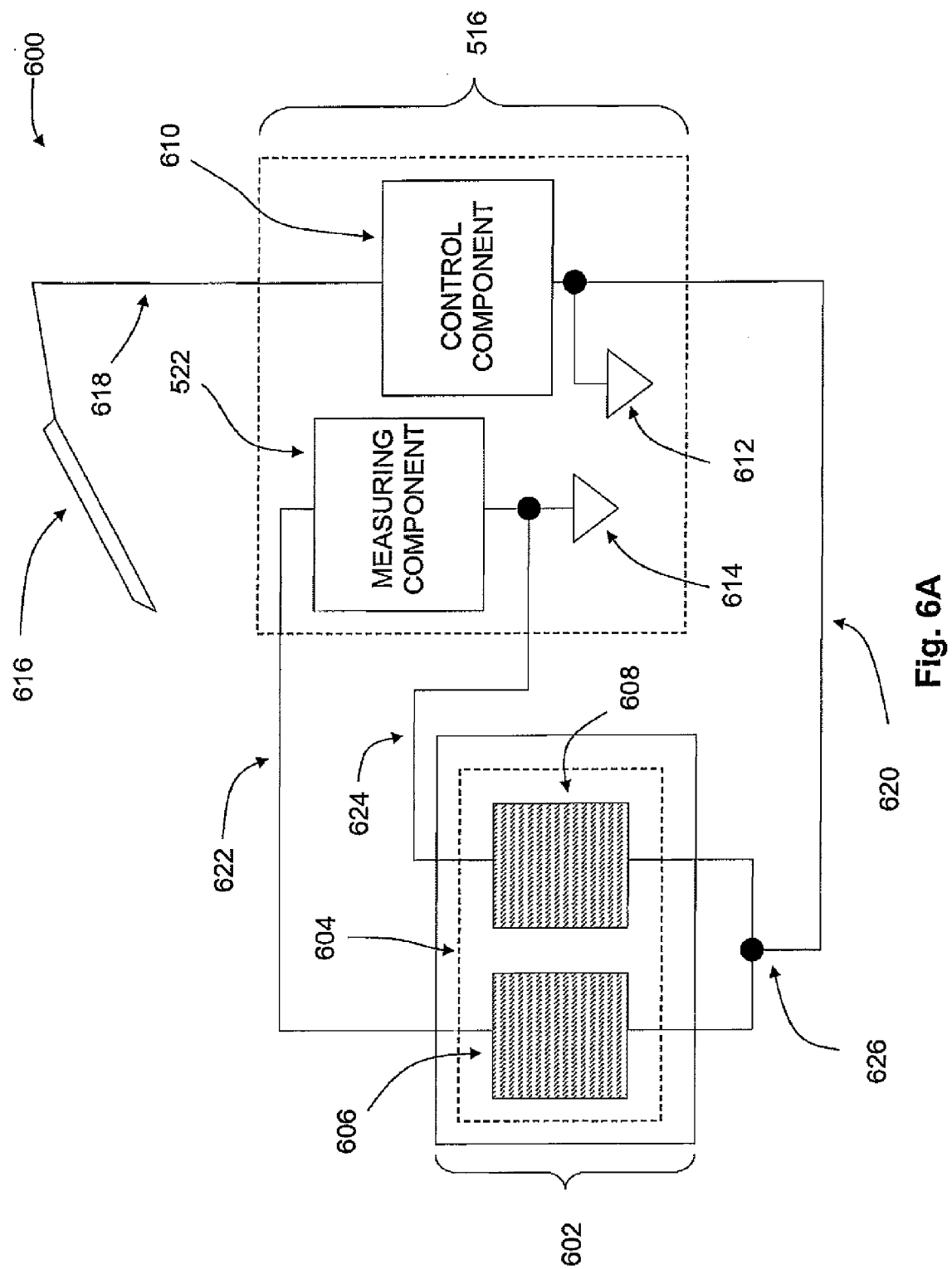
FIG. 6A is a block diagram illustrating a system that has two capacitive return electrodes for measuring contact quality in accordance with the present disclosure.

FIG. 6A shows a block diagram of system 600 according to the present disclosure that includes return pad 602 with a multiple-foil capacitive return 604 with capacitive sensing capability. More particularly, return pad 602 has a first return electrode 606 and a second return electrode 608, which operatively couples to control component 610 via return interface 626. Return interface 626 is represented by a small circular dot illustrating a return interface that may be adapted to return current from return electrodes 606 and 608. Return electrodes 606 or 608 may be made out of foil and a dielectric or other materials suitable for providing a capacitive return. Generator 516 includes both a control component 610 and a measuring component 522. Measuring component connects to return electrode 606 via 622 and to return electrode 624 via 608. The point where waveguide 622 connects to 606 and where waveguide 624 connects to return electrode 608 may be considered to be the sensing interface. The sensing interface is operatively coupled to generator 516. In system 600, measuring component 522 is located within generator 516, which is in contrast to other embodiments, such as depicted in FIG. 5B. Measuring component 522 may be inside generator 516 or otherwise may exist external to generator 516. The control component 610 produces current relative to ground reference 612 while measuring component 522 produces a test current relative to ground reference 614. Control component 610 may utilize suitable internal software, hardware, circuitry, or some combination thereof to ensure current is properly applied to a patient. Additionally or alternatively, control component 610 may also control suitable external hardware, software, circuitry, or some combination thereof to generate current for electrosurgery. For example, an external relay (not shown) may be controlled by control component 610 to physically connect or disconnect waveguide 618 from control component 610 to increase safety.

References 614 and 612 may be electrically isolated and/or an AC power source (not shown) may also be electrically isolated from both references 614 and 612, e.g. by a transformer. Surgical instrument 616 is connected to the control component 610 by a waveguide 618. A measuring current is produced by measuring component 522.

During use, return pad 602 is placed onto an area of skin utilizing an adhesive and/or conductive material to help secure return pad 602 to a patient's skin or to enhance electrical properties, e.g., to reduce contact impedance. When a surgeon applies surgical instrument 616 to another part of a patient's body, the patient completes the electrical circuit of control component 610 and may produce the desired tissue effect, e.g., cutting, coagulation, ablation etc. The return energy flows through the first foil electrode 606 and/or the second foil electrode 608 back to control component 610 via waveguide 620.

Generator 516 can take contact quality measurements of return pad 602 by utilizing measuring component 522. A test current can be created by measuring component 522 to flow from return electrode 606, through patient tissue, and to return electrode 608. Because return electrode 606 and 608 are capacitive, the measurement current should be configured with proper frequency, current, voltage, and/or wattage for capacitive purposes.

Ground references 612 and 614 may be electrically connected or isolated. For example, if references 612 and 614 were connected via a wire, then a filter (not shown) may be included at some point between return electrode 606 and reference 612 to filter out the measuring current. This can be accomplished by suitable technologies such as a notch filter, a low-pass filer, a high pass filter, a band-pass filter, a buffer, or some combination thereof. For example, if measuring component 522 were operating at frequency $f_0$ and therapeutic current were operating at frequency $f_1$ then a filter, such as a notch-filter, can attenuate frequencies at and/or near $f_0$ from traveling along waveguide 620.

Filtering, buffer, smoothing, processing or switching can be implemented within measuring component 522 or control component 610 to enhance the system. For example, the aforementioned technologies may be used to enhance noise immunity and/or provide a more efficient and accurate impedance measurement.

System 600 may also include an intelligence component (not shown) to determine when an unsafe impedance measurement has been detected. For example, an alarm may be included within the control circuitry when the contact impedance reaches a predetermined threshold, e.g., 100 ohms. The alarm may also be configured to determine if an unsafe temperature rise is predicted, which will trigger the generator 516 to disconnect waveguide 620 (and/or waveguide 620) from the current component 516. The intelligence component may be disposed inside control component 610, inside measuring component 614, or otherwise located within generator 516. The intelligence component may be implemented using suitable software, hardware, software in execution, or some combination thereof.

Figure 6B:
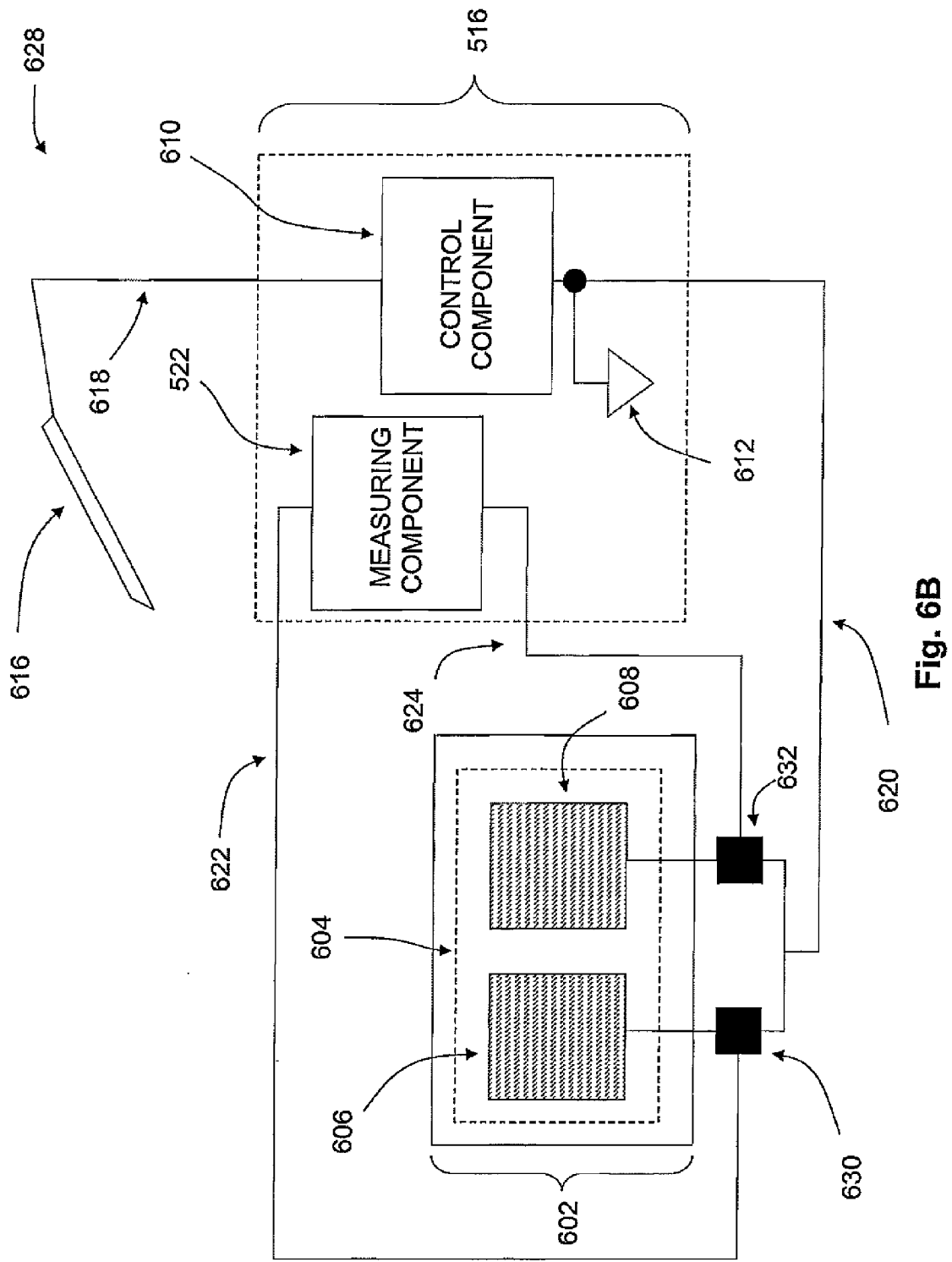
FIG. 6B is a block diagram illustrating a system that has two capacitive return electrodes for measuring contact quality by utilizing a sensing interface configured to monitor a return current difference between two capacitive return electrodes in accordance with the present disclosure.

FIG. 6B shows a block diagram of system 628 according to the present disclosure that includes return pad 602 with a multiple-foil capacitive return 604 with capacitive sensing capability. System 628 is substantially similar to system 600; however, the sensing interface is configured to utilize current monitors 630 and 632. Additionally or alternatively, measuring component 522 determines contact quality of return pad 602 by monitoring the difference between the return currents coming from return electrode 606 and 608, respectively. Because electromagnetic energy has an affinity for a lower impedance path, a peeling in either return electrode 606 or 608 would cause a reduction in the current of the return electrode undergoing peeling. The reduction in current is the result of additional contact impedance with skin of that particular return electrode. The relationships between current, impedance, and voltage are well known.

Figure 7:
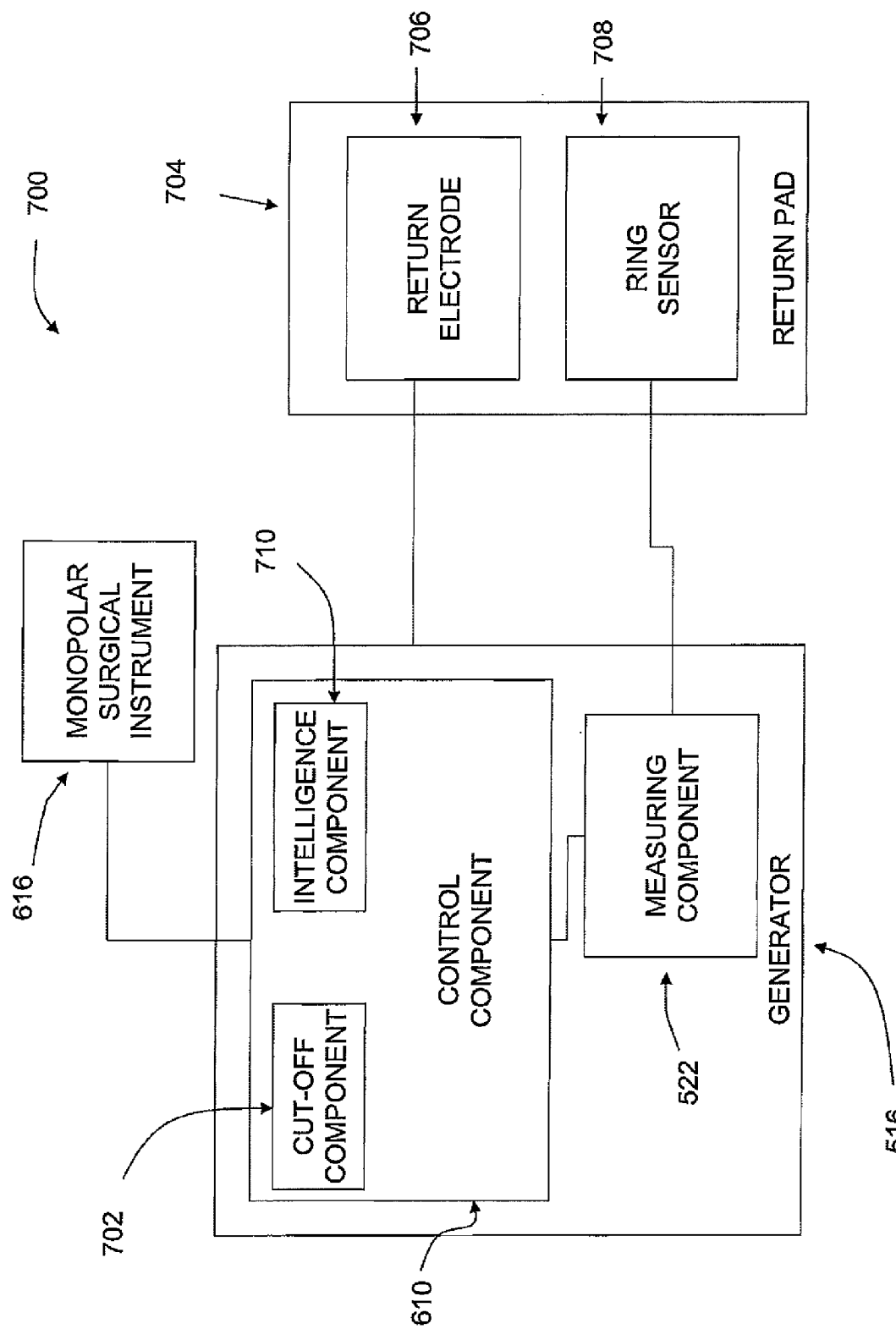
FIG. 7 is a block diagram of an electrosurgical system utilizing a return pad having a ring sensor and a return electrode in accordance with the present disclosure.

FIG. 7 shows a block diagram of another envisioned system according to the present disclosure that utilizes a return pad with a ring sensor. More particularly, system 700 includes generator 516 that has control component 610 that may generate current and measuring component 522 that may make contact quality measurements. A cut-off component 702 is also shown, which may be part of control component 610 (as shown in FIG. 7) or, alternatively, may be located elsewhere. Also, intelligence component 710 is shown as part of control component 610. Intelligence component 710 may, alternatively, be located within generator 516, within measuring component 522, or located elsewhere.

System 700 also includes return pad 704 that includes return electrode 706 and ring sensor 708. Return electrode 706 is coupled to generator 516, and ring sensor 708 is coupled to measuring component 522. A monopolar surgical instrument 616 is shown coupled to control component 610 for applying therapeutic current to a patient (not explicitly shown).

During monopolar electrosurgery, measuring component 522 may monitor contact quality by utilizing ring sensor 708. Intelligence component 710 may analyze the information from measuring component 522. An intelligence component may be located inside generator 516, inside measuring component 522, inside control component 610, or located elsewhere. An intelligence component, as mentioned above, can utilize a risk function algorithm to determine if an unsafe condition is reached in return pad 704. The risk function algorithm may be a function of therapeutic current duty cycle, therapeutic current amperage, therapeutic current settings, therapeutic current frequency, air temperature, air humidity and air composition and/or other variables that affect patient and/or surgical team safety. If an unsafe condition is reached, the intelligence component 710 communicates with the generator 516 to reduce current or otherwise take appropriate action, e.g., sounding an alarm. For example, intelligence component 710 may determine that cut-off component 702 should electrically disconnect generator 516 from return pad 704 and communicate a command; or cut-off component may electrically disconnect return electrode 706 from generator 516. Cut off component 702 may have pre-determined conditions that causes cut off component 702 to disconnect return electrode 706 or return pad 704 from generator 516, e.g., when a short occurs. Also, cut-off component may be hardware, software, software in execution, and/or circuitry, e.g., such as a microcontroller that determines that a unsafe condition is present and signals this to a relay.

Figure 8:
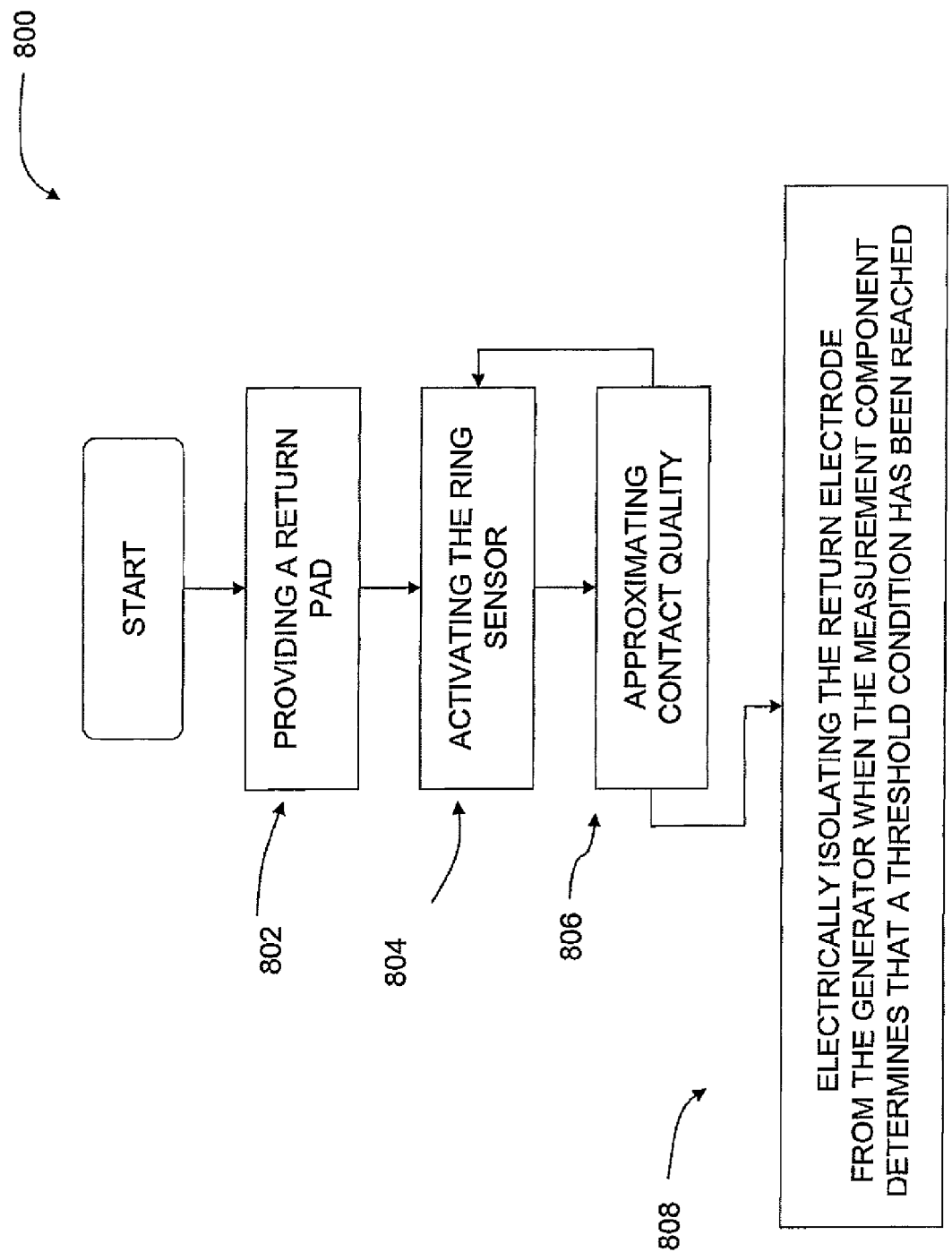
FIG. 8 is a flow chart showing one particular method in accordance with the present disclosure.

Referencing FIG. 8, the present disclosure also includes a method for monitoring contact quality of a return pad of an electrosurgical system and includes the initial step 802 of providing a return pad including a backing 102 having a top side, a bottom side, and a periphery. At least one return electrode 104 is disposed on the bottom side of the backing layer and is adapted to connect to a current generator. At least one ring sensor 110 is disposed in substantial concentric registration with the periphery of the backing and is configured to connect to a measuring component 522 that is operable to approximate contact quality of the return electrode 104 during electrosurgical application. The measuring component 522 is configured to communicate with the generator. The method also includes the steps of activating the ring sensor(s) 110 to operatively communicate with the measuring component 522 (Step 804) and approximating the contact quality of the return electrode 104 by analyzing the capacitance, impedance or resistance from the ring sensor(s) 110 (Step 806). The method may also include the step of electrically isolating the return electrode 104 from the generator when the measurement component determines that a threshold condition has been reached (Step 808).

The ring sensor(s) 110 of the providing step may include at least two partially concentric ring electrodes 106 and 108 configured to cooperate with the measuring component 522 to measure contact quality during an electrosurgical procedure and communicate contact quality to the generator. The ring sensor 110 may also include a temperature sensitive material such as a positive temperature coefficient ink.

The return pad 100 (or 200, 300, 400 or 500) of the providing step may also include a patient interface material 116 disposed between the backing layer 102 and skin. The patient interface material 116 is configured to facilitate contact quality monitoring of the return electrode 104 and may include a material selected from the group consisting of a conductive gel, a conductive adhesive, an insulating gel, an insulating adhesive, a dielectric gel, a dielectric adhesive and an insulator.

Measurements may be taken by varying electrical parameters of a test signal or current, e.g. voltage, frequency wattage, and/or current. The measurement may be made by a measuring component, e.g., measuring component 522. A control component, control component 610, may be utilized to change the surgical current based upon the measurements made by measuring component 522.

An intelligence component 710 may also be included, e.g., as part of an electrosurgical system, to monitor the conditions of return pad in act 802 and communicate the information to control component 610, to cut-off component 702, and/or otherwise to other circuitry that a pre-determined condition has occurred. For example, if contact quality has been degraded beyond an acceptable level, intelligence component 710 may cause an event to happen, such as sounding an alarm or by performing the electrically isolating step. The term "electrically isolating" may include disconnecting the pad from generator 516 or by utilizing cut-off component 702. For example, cut-off component 702 may be a relay or transistors that can electrically isolate the return pad in act 802 from generator 516.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system for measuring contact quality of a return pad, comprising:
   a return pad having a backing layer, comprising:
      at least one capacitive return electrode disposed on the bottom side of the backing layer, the at least one return electrode being adapted to connect to a return interface; and
      at least one ring sensor disposed on the at least one capacitive return electrode and in substantial concentric registration with the periphery of the at least one capacitive return electrode, the at least one ring sensor configured to connect to a sensing interface;
   a return interface adapted to return current from the at least one capacitive return electrode; and
   a sensing interface configured to monitor an impedance associated with the at least one capacitive return electrode to determine contact quality.

2. The electrosurgical system for measuring contact quality of a return pad in accordance with claim 1, further comprising an electrosurgical generator operatively associated with the return interface.

3. The electrosurgical system for measuring contact quality of a return pad in accordance with claim 1, further comprising an electrosurgical generator operatively associated with the sensing interface.

4. The electrosurgical system for measuring contact quality of a return pad in accordance with claim 1, wherein the at least one ring sensor is capacitive.

5. The electrosurgical system for measuring contact quality of a return pad in accordance with claim 1, wherein the at least one ring sensor is resistive.

6. The electrosurgical system for measuring contact quality of a return pad in accordance with claim 1, wherein the at least one ring sensor includes at least two partially concentric ring electrodes configured to cooperate with a measuring component to measure contact quality during an electrosurgical procedure and communicate contact quality to an electrosurgical generator.

7. The electrosurgical system for measuring contact quality of a return pad in accordance with claim 6, wherein the at least two partially concentric ring electrodes are disposed on the at least one capacitive return electrode.

8. The electrosurgical system for measuring contact quality of a return pad in accordance with claim 1, further comprising a patient interface material configured to be disposed between the backing layer and a patient's skin, the patient interface material configured to facilitate contact quality monitoring of the return electrode.

9. The electrosurgical system for measuring contact quality of a return pad in accordance with claim 8, wherein the interface material includes a material selected from the group consisting of a conductive gel, a conductive adhesive, an insulating gel, an insulating adhesive, a dielectric gel, a dielectric adhesive, and an insulator.

10. The electrosurgical system for measuring contact quality of a return pad in accordance with claim 1, wherein the at least one ring sensor includes a temperature sensitive material configured to sense contact quality based upon temperature.

\* \* \* \* \*